US006987565B2

(12) United States Patent
Hirahara et al.

(10) Patent No.: US 6,987,565 B2
(45) Date of Patent: Jan. 17, 2006

(54) ORGANOMETALLIC COMPOUND VAPORIZING/FEEDING SYSTEM

(75) Inventors: Kazuhiro Hirahara, Niigata-ken (JP); Takanobu Tsudera, Niigata-ken (JP); Daisuke Iwai, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 187 days.

(21) Appl. No.: 10/666,258

(22) Filed: Sep. 22, 2003

(65) Prior Publication Data

US 2004/0056044 A1   Mar. 25, 2004

(30) Foreign Application Priority Data

Sep. 19, 2002   (JP)   ............................. 2002-273094

(51) Int. Cl.
 *G01N 21/73*   (2006.01)
(52) U.S. Cl. ......................................... 356/316; 356/36
(58) Field of Classification Search ............... 356/316, 356/36
 See application file for complete search history.

(56) References Cited

U.S. PATENT DOCUMENTS

| | | | | | |
|---|---|---|---|---|---|
| 3,545,863 | A | * | 12/1970 | Ault et al. | .................. 356/313 |
| 3,586,446 | A | * | 6/1971 | Findl et al. | .................. 356/417 |
| 4,148,612 | A | * | 4/1979 | Taylor et al. | .................. 436/35 |
| 4,688,935 | A | * | 8/1987 | Barnes et al. | .................. 356/36 |
| 5,045,476 | A | * | 9/1991 | Huber | ........................ 436/81 |
| 6,473,175 | B1 | * | 10/2002 | Malczewski | ................ 356/311 |

FOREIGN PATENT DOCUMENTS

EP   0 447 747 A2   9/1991   ................. 356/316

OTHER PUBLICATIONS

Journal of Crystal Growth, 77 (1986), pp. 47-54.
Analyst, May 1990, vol. 115, pp. 535-538.
Spectrochimica Acta, vol. 44B, No. 10, pp. 1041-1048, 1989.
Journal of Analytical Atomic Spectrometry, Dec. 1994, vol. 9, pp. 1121-1128.
Journal of Electronic Materials, Vo. 18, No. 5, 1989, pp. 593-598.

* cited by examiner

*Primary Examiner*—Gregory J. Toatley, Jr.
*Assistant Examiner*—Ali Allawi
(74) *Attorney, Agent, or Firm*—Birch, Stewart, Kolasch & Birch, LLP

(57) ABSTRACT

An organometallic compound vaporizing and feeding system includes a carrier gas feed passageway connecting a carrier gas source to a container containing an organometallic compound MO and having a carrier gas mass flow controller, an MO gas passageway connecting the container to an in-line monitor for transporting the MO gas, a sample gas passageway connecting the in-line monitor to a sample inlet of an ICP spectrometer, a standard gas passageway connecting a gas cylinder filled with a calibration standard gas to the sample gas passageway and having a standard gas mass flow controller, and a diluent gas passageway connected to the standard gas passageway for passing a diluent gas for adjusting the concentration of the standard gas and having a diluent gas mass flow controller.

3 Claims, 4 Drawing Sheets

ORGANOMETALLIC COMPOUND VAPORIZING/FEEDING SYSTEM

TECHNICAL FIELD

This invention relates to a system for vaporizing and feeding an organometallic compound to an inductively coupled plasma (ICP) emission spectrometer.

BACKGROUND ART

As the crystal growth method of compound semiconductors, the metal organic chemical vapor deposition (MOCVD) method using organometallic compounds is now of great interest. The MOCVD method is one of crystal growth means commonly employed in the manufacture of epitaxial thin films of compound semiconductors. The method starts with organometallic compounds such as $(CH_3)_3Ga$, $(CH_3)_3In$ and $(CH_3)_3Al$ as the reagents, and performs crystal growth to form a thin film utilizing the thermal decomposition reaction thereof.

Since the quality of semiconductor thin films produced by the MOCVD method largely depends on the chemical purity of organometallic compounds used as the reagents, a demand for organometallic compounds of higher purity has continuously been made from the early time when the technology was developed to the present.

However, organometallic compounds are difficult to handle because of very high chemical activity and toxicity. In the current circumstance, few methods have been established for the analysis of trace impurities in organometallic compounds.

Most of the methods for the analysis of trace impurities in organometallic compounds, which have been reported so far, use an ICP emission spectrometer as the analytical instrument. In terms of the form of organometallic compounds during the ICP measurement and the method and apparatus for introducing organometallic compounds into the ICP, the technology is generally classified into the following six methods as are known in the art.

(1) Hydrolytic method: An organometallic compound is hydrolyzed to form an aqueous solution which is nebulized into aerosol and fed to an ICP torch. See Journal of Crystal Growth, 77 (1986), pp. 47–54.

(2) Solution method: After an organometallic compound is diluted with a solvent such as xylene, the mixed solution is nebulized into aerosol and fed to an ICP torch. See ANALYST, May 1990, Vol. 115.

(3) Flow injection method: Once an adduct is formed by mixing an organometallic compound with diethyl ether, it is passed through a nebulizer to form aerosol. The aerosol is then introduced into a membrane drying tube where diethyl ether is removed out of the system and only the remaining organometallic compound is fed to an ICP torch. See Spectrochimica Acta, Vol. 44B, No. 10, pp. 1041–1048, 1989.

(4) Electrothermal vaporization method: An organometallic compound is placed in a heater capable of instantaneously heating to a temperature of about 3,000° C. The vapor of organometallic compound thus generated is carried by a carrier gas and introduced directly into an ICP torch. See Journal of Analytical Atomic Spectrometry, December 1994, Vol. 9.

(5) Direct vapor introduction method: A carrier gas is blown into an organometallic compound filled in a stainless steel container, and the resulting vapor of organometallic compound is introduced directly into an ICP torch. See Journal of Electronic Materials, Vol. 18, No. 5, 1989.

(6) Exponential dilution method: A predetermined amount of organometallic compound is placed in a heater where it is heated to generate a vapor thereof, which is introduced directly into an ICP torch along with a carrier gas. See European Patent Application EP 0447747A2.

The above six methods each have advantages and disadvantages. None of them are regarded as a completed method for the analysis and introduction to ICP of organometallic compound. And yet, the direct vapor introduction method (5) is being highlighted for the reasons that (i) a change with time of the concentration of an organic impurity having a vapor pressure is directly observable, (ii) pre-treatment of organometallic compound is unnecessary, (iii) high sensitivity analysis is possible since organometallic compound can be analyzed without dilution, and (iv) only a minute quantity of a sample is necessary for measurement.

On use, however, the direct vapor introduction method has several problems. Even when the temperature of a reagent container is precisely controlled, the temperature of a carrier gas can differ from the temperature within the container. It is then difficult to control the vapor pressure of organometallic compound. Because of the lack of means for measuring the mass flow rate of organometallic compound vaporized and carried by the carrier gas, variations in feed quantity cannot be detected. While a diagram of a vapor pressure curve of an organometallic compound becomes the most important guidance in setting the feed quantity, there can be a plurality of such diagrams for the same compound. Then the temperature necessary to provide the desired feed quantity cannot be accurately determined.

SUMMARY OF THE INVENTION

An object of the present invention is to provide an organometallic compound vaporizing and feeding system which ensures that ICP analysis is possible at very high sensitivity and with reproducibility.

The present invention is directed to an organometallic compound vaporizing and feeding system wherein a carrier gas feed passageway for feeding a carrier gas from a carrier gas source and via a mass flow controller and an organometallic compound gas passageway for transporting the organometallic compound gas vaporized and carried by the carrier gas to an in-line monitor are connected to a reagent container containing an organometallic compound, and a calibration standard gas passageway having a gas mass flow controller disposed therein for controlling the flow rate of the standard gas and a dilution mass flow controller for adjusting the concentration of the standard gas as desired is connected to an organometallic compound gas passageway which is connected to a sample inlet of an ICP spectrometer via the in-line monitor. Then very high sensitivity ICP analysis is possible in a reproducible manner.

According to the present invention, there is provided an organometallic compound vaporizing and feeding system comprising (1) a reagent container containing an organometallic compound, a carrier gas source, an in-line monitor, a carrier gas feed passageway connecting the carrier gas source to the reagent container and having a mass flow controller disposed therein for controlling the flow rate of the carrier gas, (2) an organometallic compound gas passageway connecting the reagent container to the in-line monitor for transporting the organometallic compound gas vaporized and carried by the carrier gas, (3) an ICP emission spectrometer, a sample gas passageway connecting the in-line monitor to a sample inlet of the ICP spectrometer, (4) a gas cylinder filled with a standard gas for calibration, a standard gas passageway connecting the gas cylinder to the sample gas passageway and having a gas mass flow controller disposed therein for controlling the flow rate of the standard gas, and (5) a diluent gas passageway connected to the standard gas passageway downstream of the standard gas mass flow controller for passing a diluent gas for adjusting the concentration of the calibration standard gas and having a gas mass flow controller disposed therein for controlling the flow rate of the diluent gas.

In one preferred embodiment, the vaporizing and feeding system comprises a plurality of calibration standard gas cylinders, a corresponding plurality of standard gas passageways each having a gas mass flow controller disposed therein for controlling the flow rate of the corresponding standard gas, and a corresponding plurality of diluent gas passageways connected to the corresponding standard gas passageways and having diluent gas mass flow controllers disposed therein.

In another preferred embodiment, the vaporizing and feeding system further comprises a bypass passageway connected to the organometallic compound gas passageway for passing the carrier gas for diluting the concentration of organometallic compound and having a mass flow controller disposed therein for controlling the flow rate of the diluent carrier gas.

DESCRIPTION OF THE PREFERRED EMBODIMENTS

Figure 1:
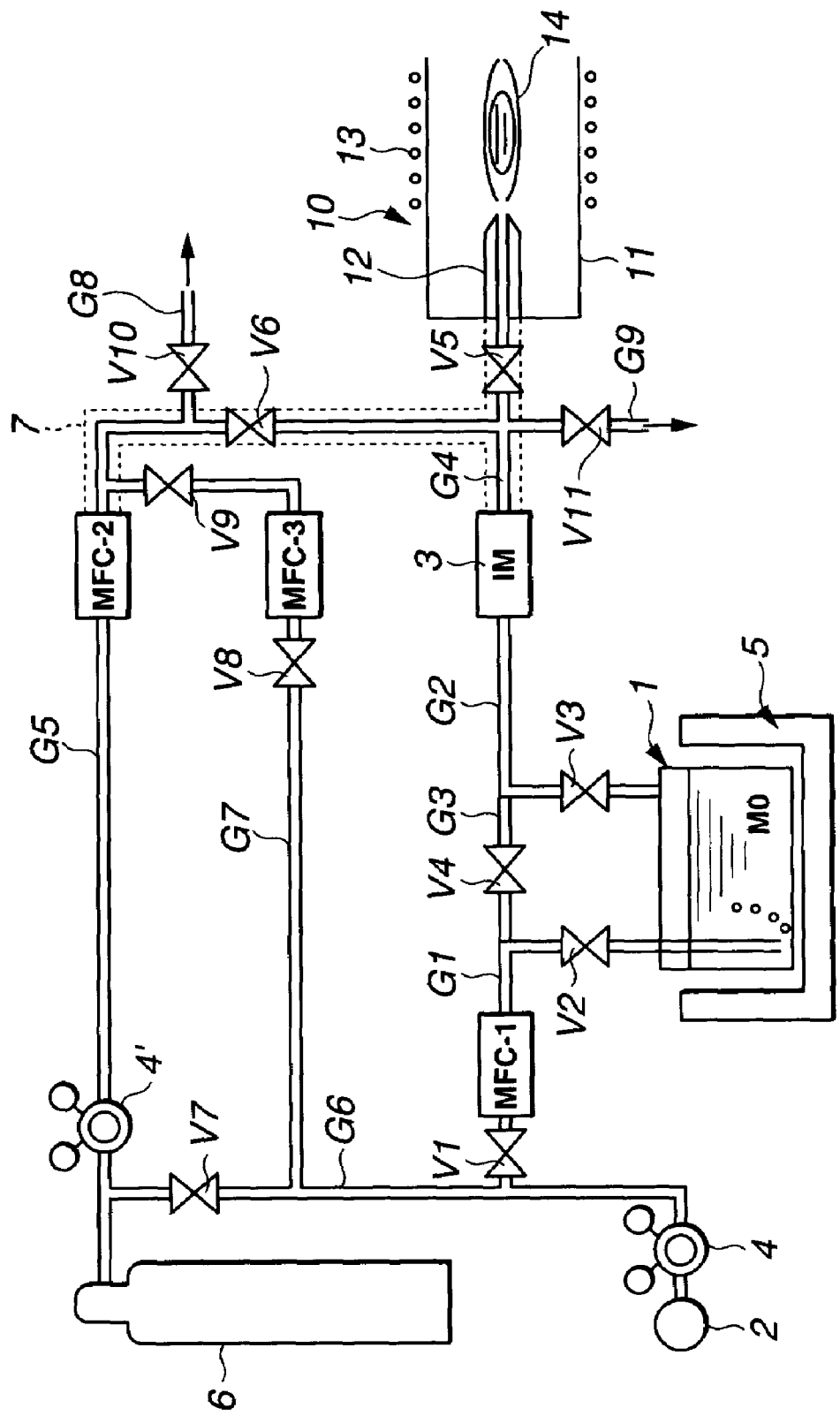
FIG. 1 is a schematic block diagram illustrating a vaporizing/feeding system according to a first embodiment of the invention.

Referring to FIG. 1, there is schematically illustrated an organometallic compound vaporizing/feeding system according to a first embodiment of the invention. The system includes a reagent container 1 containing an organometallic compound (MO), a carrier gas source 2 of argon gas or the like, and an in-line monitor 3. A carrier gas feed passageway G1 connects the reagent container 1 to the carrier gas source 2 for fluid communication. A pressure governor 4, a switching valve V1, a mass flow controller MFC-1 for controlling the flow rate of the carrier gas and a switching valve V2 are disposed in the carrier gas feed passageway G1 in this order from the upstream to downstream side. An organometallic compound gas passageway G2 connects the reagent container 1 to the in-line monitor 3 for fluid communication and has a switching valve V3 disposed therein.

The reagent container 1 is placed in a thermostat tank 5 so that the container is maintained at a temperature at which the organometallic compound is kept liquid. The end portion of the carrier gas feed passageway G1 on the container 1 side is constructed as a dip tube having an end submerged in the organometallic compound liquid. A bridge conduit G3 having a switching valve V4 disposed therein connects for fluid communication the carrier gas feed passageway G1 at a position upstream of the valve V2 to the organometallic compound gas passageway G2 at a position downstream of the valve V3.

Associated with the vaporizing/feeding system is an inductively coupled plasma (ICP) emission spectrometer 10 which includes a plasma torch 11, an injector 12, and an RF coil 13 which cooperate to produce a plasma flame 14. A sample gas passageway G4 connects an outlet of the in-line monitor 3 to a sample inlet of the ICP spectrometer 10 and has a switching valve V5 disposed therein.

Further included in the system are a gas cylinder 6 filled with a standard gas for calibration and a standard gas passageway G5 which connects for fluid communication the gas cylinder 6 to the sample gas passage G4 at a position between the in-line monitor 3 and the switching valve V5. In the standard gas passageway G5, a pressure governor 4', a gas mass flow controller MFC-2 for controlling the flow rate of the calibration standard gas, and a switching valve V6 are disposed in this order from the upstream to downstream side. A second carrier gas feed passageway G6 extends from the carrier gas source 2 to the standard gas passageway G5. More particularly, the second carrier gas feed passageway G6 has one end connected to the carrier gas source 2; a switching valve V7 is disposed in the second carrier gas passageway G6; and the second carrier gas passageway G6 has another end connected to the standard gas passageway G5 at a position upstream of the pressure governor 4'. A diluent gas passageway G7 connects the second carrier gas feed passageway G6 at a position upstream of the valve V7 to the standard gas passageway G5 at a position between the mass flow controller MFC-2 and the valve V6. A switching valve V8, a mass flow controller MFC-3 for controlling the flow rate of diluent carrier gas, and a switching valve V9 are disposed in the diluent gas passageway G7 in this order from the upstream to downstream side.

Further the system includes a purge passageway G8 which is branched from the standard gas passageway G5 at a position between the joint of the standard gas passageway G5 to the diluent gas passageway G7 and the switching valve V6 and has a switching valve V10 disposed therein. In the illustrated embodiment, another purge passageway G9 is branched from the sample gas passageway G4 at a position between the in-line monitor 5 and the switching valve V5, and a switching valve V11 is disposed therein.

The in-line monitor 3 is a device of measuring the concentration of organometallic compound gas through the organometallic compound gas passageway G2 for determining whether or not the concentration of organometallic compound gas to be fed to the ICP spectrometer is at the preset value. The in-line monitor 3 has built therein an IR absorption cell and an IR detector, and the principle of measurement is such that the organometallic compound gas is passed through the IR absorption cell, the IR absorption characteristic of the gas is measured by the IR detector, and an organometallic compound gas concentration is computed therefrom. The organometallic compound gas whose concentration has been measured by the in-line monitor 3 is directly channeled through the sample gas passageway G4 to the ICP spectrometer 10.

Figure 2:
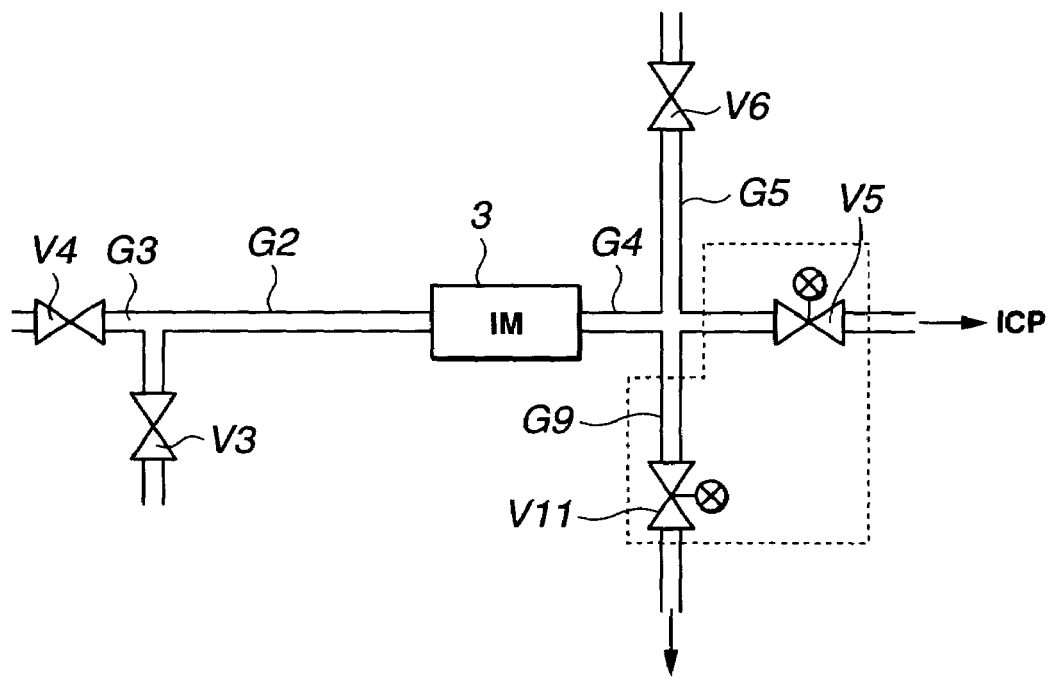
FIG. 2 is a schematic illustration of a two-throw block valve which can be used in the system of FIG. 1.

To further stabilize the concentration of the organometallic compound gas in the gas passageway, it is effective that the gas is purged through the passageway G9 for a certain period if necessary, with the valve V5 closed and the valve V11 opened. Upon switching of these valves, more or less pressure variations can occur. To reduce such pressure variations, a pneumatic two-throw block valve having switching valves V5 and V11 integrated together as shown in FIG. 2 is used. This enables instantaneous flowpath change without pressure variation.

The standard gas for calibration is necessary to quantitate the concentration of impurities remaining in the organometallic compound. It is prepared by diluting a compound containing the same elements as the impurities to be analyzed with ultra-high purity argon gas and precisely analyzing the gas concentration by a high performance analyzer such as an atmospheric pressure ionization-mass spectrometer (API-MS). The calibration standard gas is channeled through the passageway G5 having the mass flow controller MFC-2 and the passageway G4 to the ICP spectrometer 10, during which the flow rate of the gas to the ICP spectrometer can be arbitrarily changed by the mass flow controller MFC-2 whereby a calibration curve for the concentration of impurity to be analyzed (impurity concentration vs. ICP emission peak intensity) is plotted.

Figure 3:
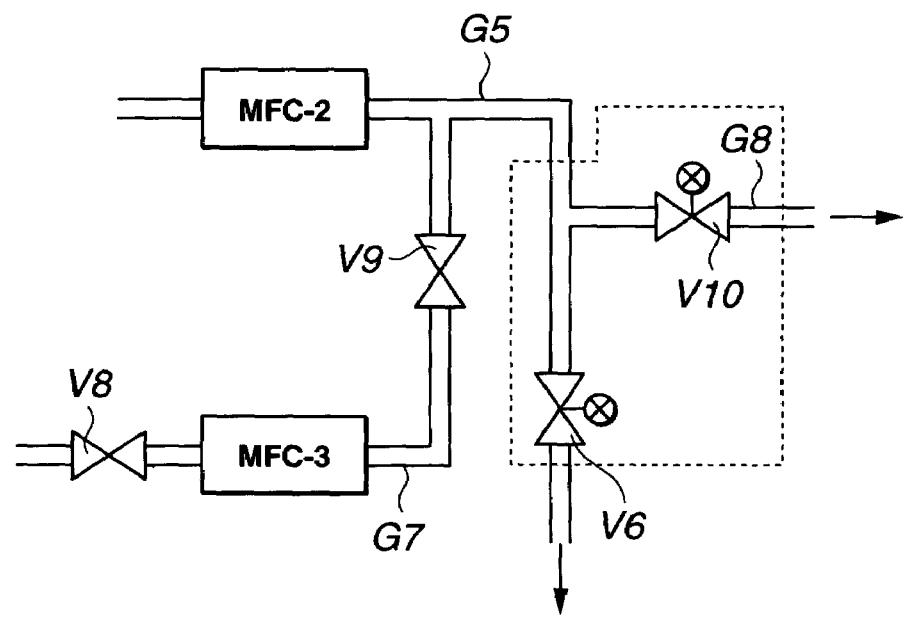
FIG. 3 is a schematic illustration of another two-throw block valve which can be used in the system of FIG. 1.

To further stabilize the concentration of the calibration standard gas in the gas passageway G5, it is effective that the gas is purged through the passageway G8 for a certain period if necessary, with the valve V6 closed and the valve V10 opened. Upon switching of these valves, more or less pressure variations can occur. To reduce such pressure variations, a pneumatic two-throw block valve having switching valves V6 and V10 integrated together as shown in FIG. 3 may be used.

As the organometallic compound gas or calibration standard gas is channeled through a passageway conduit, the organometallic compound or metal species are adsorbed to the inner wall of the conduit. Such deposits can exert a memory effect to adversely affect the analytical results. To minimize or eliminate such influence, a heating means in the form of a tape heater 7 is preferably attached to a conduit section of the sample gas passageway G4 extending from the in-line monitor 3 to the ICP spectrometer 10, and a conduit section of the standard gas passageway G5 downstream of the mass flow controller MFC-2.

The passageways G6 and G7 may be used for other purposes. It is effective to flow the carrier gas as the purging gas through the diluent gas passageway G7 by way of the valve V8, mass flow controller MFC-3 and valve V9, for the purpose of re-adjusting the concentration of the calibration standard gas or instantaneously flushing away the memory effect within the conduit. The second carrier gas feed passageway G6 connecting the carrier gas source 2 to the standard gas passageway G5 via the valve V7 may be used as a purging line when the calibration standard gas is exchanged.

Figure 4:
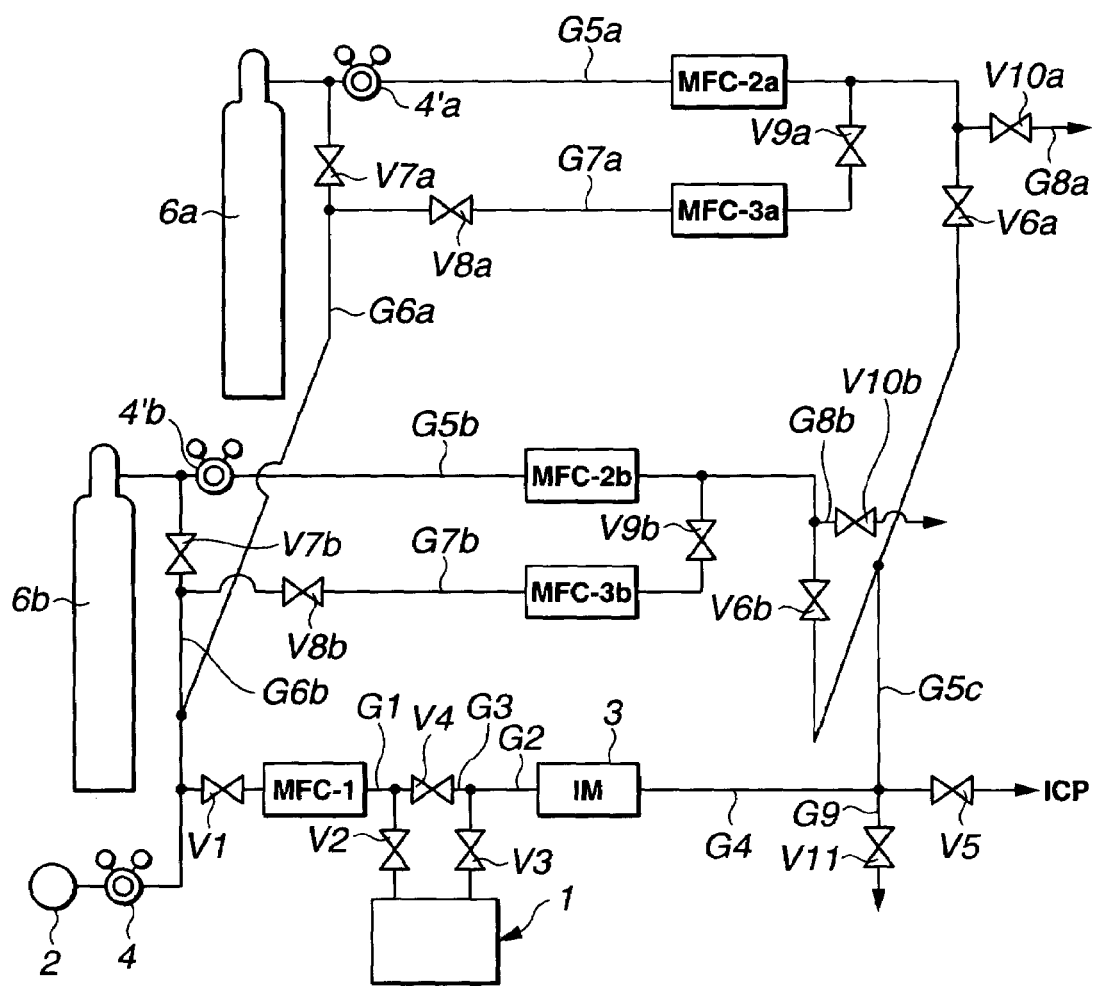
FIG. 4 is a schematic block diagram illustrating a portion of the vaporizing/feeding system according to a second embodiment of the invention.

FIG. 4 illustrates an organometallic compound vaporizing/feeding system according to a second embodiment of the invention. The system includes two gas cylinders 6a and 6b for containing two species of calibration standard gas, respectively. The gas cylinders 6a and 6b are connected to one ends of standard gas passageways G5a and G5b, which have pressure governors 4' and 4', gas mass flow controllers MFC-2a and MFC-2b for controlling the flow rate of standard gas, and switching valves V6a and V6b, respectively. The other ends of standard gas passageways G5a and G5b are connected to one end of a standard gas feed passageway G5c which has another end connected to the sample gas passageway G4 upstream of the switching valve V5.

Diluent gas passageways G7a and G7b connect carrier gas passageways G6a and G6b to the standard gas passageways G5a and G5b, respectively. More particularly, switching valves V8a and V8b, diluent gas mass flow controllers MFC-3a and MFC-3b, and switching valves V9a and V9b are disposed in the diluent gas passageways G7a and G7b. The carrier gas passageways G6a and G6b connect the carrier gas source 2a to the standard gas passageways G5a and G5b upstream of the pressure governors 4' and 4' and have switching valves V7a and V7b disposed therein. The diluent gas passageways G7a and G7b are connected between the carrier gas passageways G6a and G6b at a position upstream of the switching valves V7a and V7b and the standard gas passageways G5a and G5b at a position between the mass flow controllers MFC-2a, MFC-2b and the valves V6a, V6b. From the passageways G5a and G5b are branched purge passageways G8a and G8b having valves V10a and V10b. The rest of the system is the same as in FIG. 1.

It is understood that more than two species of calibration standard gas may be used, and in such a case, their cylinders are connected to a corresponding number of standard gas passageways.

Since the calibration standard gases correspond to the types of impurity to be analyzed, they are finally needed in the number of elements to be analyzed. For simplification of the system, a standard gas for multiple element calibration should be prepared by charging a single pressure container with all metal-containing compounds as subjects of measurement. However, some compounds can form non-volatile compounds or change to other compounds through chemical reaction. Then the compounds must be divided into certain groups each consisting of those compounds which remain intact even when mixed together. This necessitates a plurality of calibration standard gases and a corresponding plurality of feed passageways. With the manipulation of ICP and other factors taken into account, the number of calibration standard gases, the number of gas mass flow controllers or the number of gas passageways is desirably 2 to 5.

It is noted that the flow rate of the calibration standard gas through the mass flow controller MFC-2 is preferably 0.1 to 100 ml/min, more preferably 1 to 10 ml/min.

Figure 5:
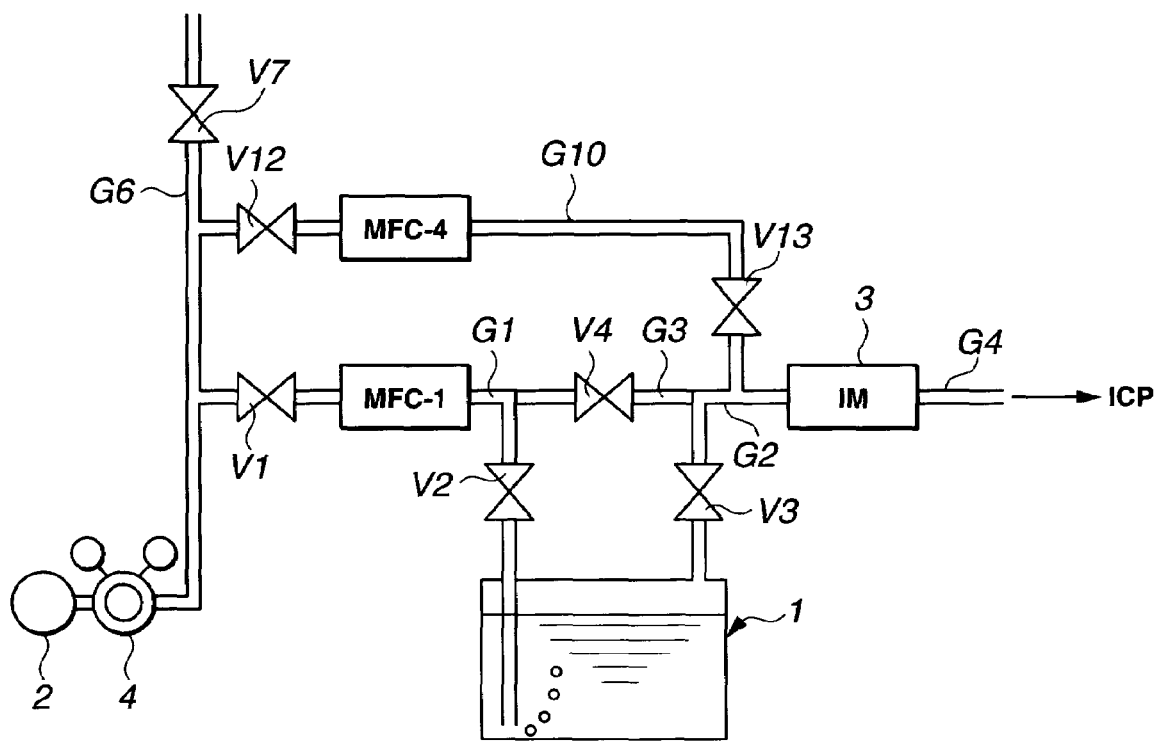
FIG. 5 is a schematic block diagram illustrating a portion of the vaporizing/feeding system according to a third embodiment of the invention.

FIG. 5 illustrates an organometallic compound vaporizing/feeding system according to a third embodiment of the invention. The system includes a bypass passageway G10 which is branched from the carrier gas feed passageway G6 to the organometallic compound gas passageway G2 for feeding the carrier gas for diluting the concentration of the organometallic compound gas flowing through the passageway G2. In the bypass passageway G10, a switching valve V12, a mass flow controller MFC-4 for controlling the flow rate of the carrier gas for dilution, and a switching valve V13 are disposed from the upstream to downstream side. A downstream end of the bypass passageway G10 is connected to the organometallic compound gas passageway G2 at a position downstream of the joint to the bridge conduit G3. The rest of the system is the same as in FIG. 1.

Now the operation of the system is described. The carrier gas is adjusted to a predetermined pressure by the pressure governor 4. Then the switching valve V1 is opened, and the carrier gas is passed through the mass flow controller MFC-1 in which the flow rate has previously been set. After it is confirmed that the switching valves V2 and V3 are closed, the switching valves V4 and V5 are opened. Then the carrier gas is channeled to the injector of the ICP spectrometer 10 through the gas passageways G1, G3 and G4 by way of the in-line monitor 3. The result of ICP measurement performed in this state is a blank.

After it is confirmed that the temperature of the container 1 within the thermostat tank 5 is at a predetermined level, the switching valve V3 is first opened, the switching valve V2 is then opened, the switching valve V4 is then moderately closed. Then the carrier gas is transported from the source 2 to the container 1 through the dip tube and vigorously bubbled into the organometallic compound in the container 1 for vaporization. The organometallic compound gas thus vaporized and carried by the carrier gas is transported through the organometallic compound gas passageway G2 to the in-line monitor 3 to determine whether the organometallic compound gas concentration is a predetermined concentration. The organometallic compound gas is transported through the passageway G4 to the injector of the ICP spectrometer 10 where it is analyzed.

To accurately quantitate the amount of an impurity in the organometallic compound gas, the calibration standard gas can be introduced to the ICP spectrometer 10 by way of the mass flow controller MFC-2 and through the passageways G5 and G4.

The organometallic compound (MO) of interest in ICP analysis is not particularly limited as long as it is used as a reagent for MOCVD. The invention is effective in microanalysis for so-called compound semiconductor materials such as III–V Group and II–VI Group semiconductors.

Illustrative non-limiting examples of organometallic compounds include trimethyl (or ethyl) gallium, trimethyl (or ethyl) indium, trimethyl (or ethyl) aluminum, dimethyl (or ethyl) zinc, tert-butyl phosphine, tert-butyl arsine, cyclopentadienyl magnesium, and pentamethylcyclopentadienyl magnesium. All organometallic compounds, organic compounds, metal hydrides and metal halides are analytes as long as they have any vapor pressure at normal temperature and atmospheric pressure. It is understood that analysis is essentially impossible if a metal impurity as a subject of measurement has no vapor pressure and cannot be transported by the carrier gas.

The in-line monitor 3 is a device of measuring the concentration of organometallic compound gas through the organometallic compound gas passageway G2 for determining whether or not the concentration of organometallic compound gas to be fed to the ICP spectrometer is at the preset value. To further stabilize the concentration of the organometallic compound gas in the gas passageway, as previously described, it is effective that the gas is purged through the passageway G9 for a certain period if necessary, with the valve V5 closed and the valve V11 opened. Upon switching of these valves, more or less pressure variations can occur, which may be effectively reduced using a pneumatic two-throw block valve having switching valves V5 and V11 integrated together as shown in FIG. 2.

The standard gas for calibration is necessary to quantitate the concentration of impurities remaining in the organometallic compound. The calibration standard gas is channeled through the passageway G5 having the mass flow controller MFC-2 and the passageway G4 to the ICP spectrometer 10.

To further stabilize the concentration of the calibration standard gas in the gas passageway G5, as previously described, it is effective that the gas is purged through the passageway G8 for a certain period if necessary, with the valve V6 closed and the valve V10 opened. Upon switching of these valves, more or less pressure variations can occur, which may be effectively reduced using a pneumatic two-throw block valve having switching valves V6 and V10 integrated together as shown in FIG. 3.

For the purpose of re-adjusting the concentration of the calibration standard gas or instantaneously flushing away the memory effect within the conduit, it is effective to flow the carrier gas as the purging gas through the diluent gas passageway G7 by way of the valve V8, mass flow controller MFC-3 and valve V9. The second carrier gas feed passageway G6 connecting the carrier gas source 2 to the standard gas passageway G5 via the valve V7 may be used as a purging line when the calibration standard gas is exchanged.

Described below is an example wherein the system is operated.

First, the plasma torch of ICP-AES is ignited, confirming steady burning of a plasma. The switching valve V4 is opened, and the carrier gas (argon) is channeled at a flow rate controlled by the gas mass flow controller MFC-1. The flow rate of the carrier gas is generally 5 to 1,000 ml/min, preferably 10 to 600 ml/min although it varies with a particular type of organometallic compound used. If the burning of argon plasma becomes unstable or if it becomes necessary to largely vary the organometallic compound concentration, the carrier gas for dilution is fed through the dilution mass flow controller MFC-4 as shown in FIG. 5, preferably at a flow rate of 10 to 2,000 ml/min, more preferably 50 to 800 ml/min.

The main valve V3 of the reagent container 1 is opened, after which the main valve V2 is moderately opened. The switching valve V4 is closed in this state, immediately after which the mass flow controller MFC-1 starts flow rate control to feed the carrier gas at a predetermined flow rate to the container 1. The organometallic compound vaporized and carried by the carrier gas is channeled through the organometallic compound gas passageway G2 and by way of the valve V3 to the in-line monitor 3 where the concentration of the organometallic compound gas is accurately measured. The preferred organometallic compound gas concentration is expressed by a flow rate of 0.001 to 1 g/min, more preferably 0.01 to 0.1 g/min.

The organometallic compound gas is then introduced to ICP through the gas passageway G4. To further stabilize the concentration of the organometallic compound gas within the gas passageway, it is effective that gas purging from the passageway G9 is performed for about 2 to 5 minutes, with the switching valve V5 closed and the switching valve V11 opened.

In this way, the organometallic compound gas whose concentration and flow rate are explicitly predetermined is fed to the ICP spectrometer. Then fast, high precision ICP analysis is possible with very high safety to humans.

The compound which can be used in the calibration standard gas may be a compound which contains a target metal, has an appropriate vapor pressure, and does not undergo complex chemical changes even when a plurality of compounds are admixed. An exemplary preferred compound is tetramethylsilane when silicon is the impurity to be detected and tetramethylgermane when germanium is the impurity to be detected. The gas with which the compound is diluted is most preferably argon, and its concentration is typically 0.1 to 1,000 ppm, more typically 1 to 200 ppm. The calibration standard gas should be checked for a precise metal concentration by a high performance analyzer such as API-MS.

As the calibration standard gas is channeled through the passageways G5 and G4 to the ICP spectrometer by way of the mass flow controller MFC-2 and valve V6, the emission peak intensities corresponding to respective elements are measured. Using calibration curves of peak intensity vs. standard gas concentration, the concentrations of impurities in the organometallic compound gas can be accurately determined.

It is noted that the chemical reaction between the compounds used as the standard gases can be prevented by providing two separate circuits for two calibration standard gases as shown in FIG. 4.

In the organometallic compound vaporizing and feeding system of the invention, a carrier gas is introduced into a reagent container filled with an organometallic compound at a flow rate controlled by a mass flow controller, to vaporize the organometallic compound. The organometallic compound gas is measured for concentration by an in-line monitor before entry to an ICP spectrometer. The concentration of the organometallic compound gas fed to the ICP spectrometer and the impurity concentration can always be monitored.

The continuously varying feed quantity of the organometallic compound and variations in impurity concentration can be directly observed. Thus the organometallic compound gas having an accurate concentration can always be introduced to the ICP spectrometer.

Since a calibration standard gas can be fed directly to the ICP spectrometer, qualitative and quantitative analyses can be performed in-line on the concentrations of impurities remaining in the organometallic compound gas.

Since a plurality of standard gases for calibration can be generated at the same time, quantitative and qualitative analyses of a wide variety of impurities can be instantaneously performed. The invention eliminates the cumbersome and dangerous operation of sampling the liquid organometallic compound by means of a dispenser such as a syringe, significantly increasing the safety to humans and avoiding the risk of contamination during the sampling operation. ICP analysis using minute quantities of expensive organometallic compound is possible at very high sensitivity and in a reproducible manner.

As a result, very high sensitivity ICP analysis is possible in a highly safe and reproducible manner.

Japanese Patent Application No. 2002-273094 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An organometallic compound vaporizing and feeding system comprising
   (1) a reagent container containing an organometallic compound, a carrier gas source, an in-line monitor, a carrier gas feed passageway connecting said carrier gas source to said reagent container and having a mass flow controller disposed therein for controlling the flow rate of the carrier gas,
   (2) an organometallic compound gas passageway connecting said reagent container to said in-line monitor for transporting the organometallic compound gas vaporized and carried by the carrier gas,
   (3) an ICP emission spectrometer, a sample gas passageway connecting said in-line monitor to a sample inlet of said ICP spectrometer,
   (4) a gas cylinder filled with a standard gas for calibration, a standard gas passageway connecting said gas cylinder to said sample gas passageway and having a gas mass flow controller disposed therein for controlling the flow rate of the standard gas, and
   (5) a diluent gas passageway connected to said standard gas passageway downstream of the standard gas mass flow controller for passing a diluent gas for adjusting the concentration of the calibration standard gas and having a gas mass flow controller disposed therein for controlling the flow rate of the diluent gas.

2. The vaporizing and feeding system of claim 1, comprising a plurality of calibration standard gas cylinders, a corresponding plurality of standard gas passageways each having a gas mass flow controller disposed therein for controlling the flow rate of the corresponding standard gas, and a corresponding plurality of diluent gas passageways connected to the corresponding standard gas passageways and having diluent gas mass flow controllers disposed therein.

3. The vaporizing and feeding system of claim 1, further comprising a bypass passageway connected to said organometallic compound gas passageway for passing the carrier gas for diluting the concentration of organometallic compound and having a mass flow controller disposed therein for controlling the flow rate of the diluent carrier gas.

* * * * *